United States Patent [19]

Wu

[11] 4,325,151
[45] Apr. 20, 1982

[54] COOLING PILLOW WITH HEAT DISSIPATOR

[76] Inventor: An C. Wu, FL. 4-1, No. 58, Hsin-Yi Rd., Section 4, Taipei, Taiwan

[21] Appl. No.: 129,809

[22] Filed: Mar. 12, 1980

[51] Int. Cl.³ ............................................. A47G 9/00
[52] U.S. Cl. .......................................... 5/441; 5/421; 5/442; 165/46; 165/185
[58] Field of Search ................... 5/421, 422, 441, 442, 5/434, 436; 297/180; 165/46, 185

[56] References Cited

U.S. PATENT DOCUMENTS

| | | | |
|---|---|---|---|
| 3,882,873 | 5/1975 | Arango | 165/46 |
| 3,900,910 | 8/1975 | Nakata | 5/442 |
| 4,060,276 | 11/1977 | Lindsay | 297/180 |
| 4,236,264 | 12/1980 | Britzman | 5/441 |

*Primary Examiner*—Alexander Grosz
*Attorney, Agent, or Firm*—Karl W. Flocks; Sheridan Neimark

[57] ABSTRACT

Cooling pillow with heat dissipator comprising a head-resting surface which is temperature maintained by thermally transferring heat released by the user to and through a heat conducting metal plate in contact with a wet absorbent medium receiving water from a water tank in a ventilated enclosure.

6 Claims, 3 Drawing Figures

U.S. Patent
Apr. 20, 1982
4,325,151
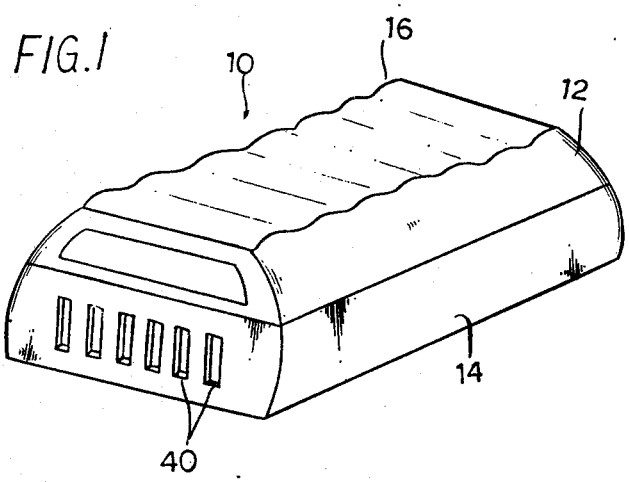
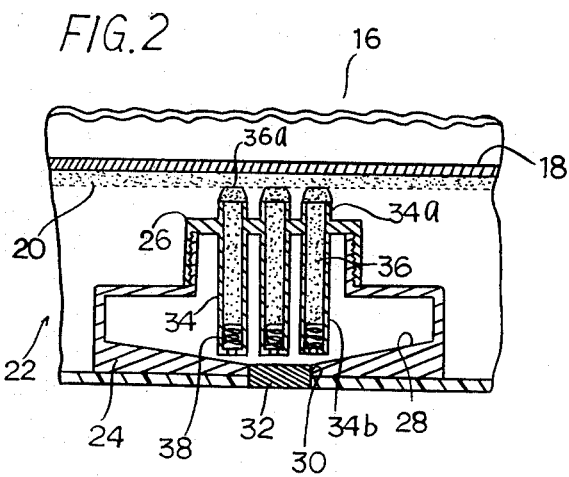
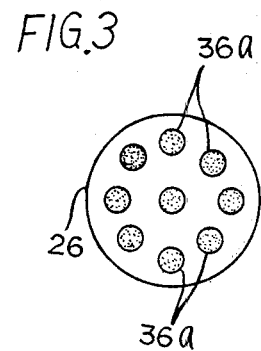

COOLING PILLOW WITH HEAT DISSIPATOR

BACKGROUND OF THE INVENTION

This invention relates to a cooling pillow with heat dissipator and more particularly to a cooling pillow construction wherein its heat dissipator serves to maintain the pillow at a pleasant or fixed temperature when receiving heat from the user's head resting on the pillow.

In the past, various types of pillows were utilized which were stuffed with cotton, green bean shells and other stuffing materials. Also in the past, there existed inflatable plastic envelopes in the shape of pillows. These prior pillows were generally air-tight and did not include heat releasing or dissipating devices, so that when in use, these prior pillows stored heat, resulting in higher temperatures which made the user uncomfortable and interfered with sound sleep at night, particularly in the summer.

It is well recognized that the brain is an element of the human body of the utmost importance. In order to keep the mind and body in good balance, the brain should be kept at a comfortable temperature,. This is particularly true in the present era where competition exists in connection with all activities. It is clear that the brain should be in a comfortable ambient. Otherwise, under adverse conditions continued for an extended period of time, the brain may be subject to many types of diseases with the resulting lowering of the general health of people.

SUMMARY OF THE INVENTION

An object of the instant invention is to depart from the structure of the prior pillows and to provide a relatively simple cooling pillow with heat releasing device or dissipator which serves to maintain the temperature of the pillow in such fashion that the brain of the user is kept comfortable.

In accordance with the present invention the cooling pillow with heat releasing device or dissipator includes two main parts. First, it includes an upper envelope or cushion which may be made of an elastic material or rubber and be filled with air or cold water. The upper portion of the cushion on which the head of the user may rest has a surface which is undulated or in the form of waves. Second, it includes the heat releasing device or heat dissipator. This heat dissipator is a cooling apparatus which serves to transfer heat from the cushion by removing it and passing it on to the atmosphere. This heat releasing device or heat dissipator comprises a metal or aluminum plate of good thermal conductivity, an absorbent cloth or fabric in the form of a lamina in contact with and beneath said plate, a cooling means communicating with said absorbent fabric including a water tank and a cover therefor, and a plurality of open-ended tubes or pipes, each containing water absorbing material in the shape of bars, said pipes or tubes extending above, through, and below said cover, the top of the absorbent material in said tubes being in contact with said absorbent cloth or fabric which, in turn, contacts said plate. The lower ends of said open-ended pipes or tubes extend into the water tank. The upper ends of the absorbent material in each of the pipes or tubes has a tip which is cap-shaped and extends sufficiently above each pipe or tube to effectively make good contact with the absorbent cloth or fabric lamina which, in turn, is in contact with and beneath the metal or aluminum plate of good thermal conductivity.

In accordance with the invention there is provided a cooling pillow with a heat dissipator or heat releasing device wherein the envelope of the cushion may be filled with cold water and the water tank may be filled with cold water.

When the head of the user transmits heat to the cushion, the heat will be transferred to the cold water in the cushion which transfers heat to the metal or aluminum plate which, in turn, transfers heat to the absorbent cloth or fabric lamina in contact with and beneath said plate. The absorbent cloth or fabric beneath the plate is always kept wet by water from the water tank into which the absorbent material within the pipes or tubes extends. It therefor will be understood that this construction is effective to maintain a pleasant or specific temperature range on the upper surface of the cushion which includes the head-resting area or head osculating plane. It will be further understood that in accordance with the invention, the head-resting area of the upper surface of the cushion is undulated or in the form of waves so that the head of the user will be in only partial contact and that therefor there will be ventilating channels provided by the troughs of the waves or undulated form.

It is a further object of the instant invention to provide a novel cooling pillow with heat dissipator which is effective to maintain a comfortable temperature range on the upper pillow surface. Such construction efficiently makes for recovery from tiredness and when used for a long time will assist or be helpful in connection with recoveries from nervous breakdown, cerebral hemorrhage, heart disease, insomnia, high blood pressure and like disorders.

The construction of the instant invention may be used in winter and in order to keep the pillow from becoming too cold, instead of putting cold water in the envelope of the cushion, it can be filled with air.

BRIEF DESCRIPTION OF THE DRAWINGS

Other objects, features and advantages of the present invention will become apparent from a study of the written description and the drawings in which:

FIG. 1 is a view in perspective of the cooling pillow with heat dissipator or heat releasing device.

FIG. 2 is an enlarged fragmentary vertical section through the cooling pillow with heat dissipator or heat releasing device.

FIG. 3 is a top or plan view of the cover of the water tank of the heat dissipator or heat releasing device.

DETAILED DESCRIPTION OF THE PREFERRED EMBODIMENT

Referring to the drawings, the cooling pillow 10 with heat dissipator or heat releasing device includes as an upper part the elastic or rubber envelope 12 and it also includes as a lower part the heat dissipator or heat releasing device. 14. The cushion 12 is provided with a filling opening, not shown, for the purpose that water or air may be put into the cushion 12. The upper surface of the cushion 12 is the head-contacting area 16 which is in undulated form or in the form of waves. In contact with the lowest surface of water or air within the cushion 12 is the metal or aluminum cooling plate 18. This plate 18 is a part of the heat dissipator or heat releasing device 14 and it serves to receive heat from the medium, water or air, within the cushion 12 and the head-contacting area 16.

An absorbent cloth or fabric 20 is in the form of a lamina underneath and in contact with the metal or aluminum cooling plate 18 of the heat dissipator or heat releasing structure generally designated by the reference numeral 22 in FIG. 2, which is part of and is included in the entire heat dissipator and heat releasing device even more generally indicated by the reference numeral 14 in FIG. 1.

Referring specifically to FIGS. 2 and 3, the cooling structure 22 includes a water tank 24 and a cover 26. The water tank 24 has an inwardly and downwardly sloping or declivitous tank bottom 28. The center of the tank bottom 28 has an opening 30, so that water may be poured therein, and a closure therefor or stopper 32. The cover 26 has a plurality of open-ended pipes or tubes 34, each of which has a tip 34a which extends above the cover 26, and a lower part 34b which extends into the water tank 24. Inside each tube or pipe 34 there is a highly absorbent material or bar 36. The upper end of this highly absorbent material or bar 36 or upper tip of this material or bar is cap-shaped and is indicated by the reference numeral 36a. The cap-shaped tips 36a which extend above the tubes or pipes 34 contact the absorbent cloth or fabric 20 in the form of lamina extending beneath and in contact with the metal or aluminum cooling plate 18 which is of good thermal conductivity. Associated with the lower end of each highly absorbent material or bar 36 is a spring 38 which urges this highly absorbent material or bar 36 upwardly to maintain constant contact with the absorbent cloth or fabric 20.

After the water tank 24 is filled with water, the highly absorbent material 36 in the pipes or tubes 34 will become wet and in turn wet the absorbent cloth or fabric 20 which is beneath the metal or aluminum plate 18. The absorbent cloth or fabric 20 is always wet in order to maintain good thermal transfer from the metal or aluminum plate 18.

During the summer, when it is hot, in utilizing the cooling pillow 10 with heat dissipator or heat releasing device 14 of the instant invention the cushion 12 may be filled with cool water and the water tank 24 may also be filled with cool water. When heat from the head of the user is transferred to the upper surface of the cushion 12, which upper surface is designated as the head-contacting or osculating plane 16, the heat will be transferred immediately to the cool water in the cushion 12 and, in turn, transferred to the metal or aluminum plate 18 which, in turn, transfers the heat to the heat dissipator structure 22 so that the pillow is maintained at a comfortably low temperature in a specific temperature range and the brain of the user will be kept comfortable and the user may have a sound sleep.

In the winter, in order to keep the air cushion 12 from becoming too cold, it may be filled with air instead of water. Again, referring to FIG. 1, in order to insure that the heat dissipator or heat releasing device 14 is operating efficiently in the circumstance of its location, it is provided with an enclosure ventilated by openings 40. Accordingly it will be understood that the heat dissipator or heat releasing device 14 including the heat releasing structure 22 is well ventilated.

Though the invention has been described with respect to a specific preferred embodiment thereof, many variations and modifications will become apparent to those skilled in the art. It is therefore the intention that the appended claims be interpreted as broadly as possible in view of the prior art to include all such variations and modifications.

What is claimed is:

1. A cooling pillow with heat dissipator essentially including an upper cushion in the form of an elastic envelope and lower heat dissipator, said heat dissipator comprising a metal plate of good thermal conductivity, an absorbent fabric lamina in contact with and beneath said plate, a cooling means communicating with said absorbent fabric including a water tank and a cover therefor and a plurality of open-ended tubes containing absorbent material, said tubes extending above, through, and below said cover, the top of the absorbent material in said tubes being in contact with said absorbent fabric which contacts said plate and the lower ends of said tubes extending into said water tank.

2. A cooling pillow in accordance with claim 1 wherein the envelope of the upper cushion is made of rubber.

3. A cooling pillow in accordance with claim 1 or 2, wherein the plate of good thermal conductivity is aluminum.

4. A cooling pillow in accordance with claim 1 or 2, wherein the top of the upper cushion is formed with an undulated area on which the head of the user may rest.

5. A cooling pillow in accordance with claim 1 wherein the plate of good thermal conductivity is of aluminum and the lower ends of said tubes are fitted with springs to urge and maintain the upper tips of the absorbent material in the tubes into contact with said absorbent fabric lamina.

6. A cooling pillow in accordance with claim 1 or 5, wherein said cooling means is enclosed within a ventilated housing.

* * * * *